United States Patent [19]

Bruera

[11] Patent Number: 4,904,243

[45] Date of Patent: Feb. 27, 1990

[54] DEVICE FOR SELF-ADMINISTRATION OF DRUGS OR THE LIKE

[76] Inventor: Eduardo Bruera, 140 Michener Park, Edmonton, Alberta, Canada, T6H 4M4

[21] Appl. No.: 217,349

[22] Filed: Jul. 11, 1988

[51] Int. Cl.⁴ .............................................. A61M 5/00
[52] U.S. Cl. ..................... 604/183; 604/208
[58] Field of Search ................ 604/181–185, 604/208, 209, 210

[56] References Cited

U.S. PATENT DOCUMENTS

| | | | |
|---|---|---|---|
| 2,645,224 | 7/1953 | Beebe | 604/183 |
| 4,022,207 | 5/1977 | Citrin | 604/209 |
| 4,051,852 | 10/1977 | Villari | 604/183 |
| 4,210,173 | 7/1980 | Choksi et al. | 604/186 X |

*Primary Examiner*—Dalton L. Truluck
*Attorney, Agent, or Firm*—Foley & Lardner, Schwartz, Jeffery, Schwaab, Mack, Blumenthal & Evans

[57] ABSTRACT

The device is carried on the body of a patient under treatment and is associated with a container to contain the fluid to be administered to and by said patient and a remote needle to inject the fluid in the patient. The device comprises a one way valve system; a first flexible tube connecting the valve to said container and a second flexible tube connecting down-stream side of the valve to the needle. The one way valve system prevents the back-flow of blood from the patient or administered fluid, and the out flow of fluid back into the container. A calibrated syringe including a plunger is mounted in a syringe holder on the upstream side of the valve system. The syringe holder acts on the plunger to withdraw a predetermined portion of fluid from the container and thereafter to inject the predetermined portion to the patient.

1 Claim, 2 Drawing Sheets

DEVICE FOR SELF-ADMINISTRATION OF DRUGS OR THE LIKE

BACKGROUND OF THE INVENTION (1.) Field of the Invention

This invention relates to a device for subcutaneous self-administration of drugs or the like. More particularly, the present invention is concerned with a device which is attached to a standard disposable syringe and makes it safe for a patient to inject himself for periods of up to one week without changing the syringe.

(2.) Description of Prior Art

Home management of cancer patients is the most rapidly growing area of oncology. Eighty percent of these patients need analgesics, and of those more than half will need injections before death. Currently available devices are extremely expensive and difficult to operate. Therefore, they are not used by most centres. At the best, there are portable, battery operated pumps, which are usually very expensive and are difficult to operate.

SUMMARY OF INVENTION

It is an object of the present invention to provide a device which allow patients to self administer drugs with a cheap disposable device, instead of using battery operated, computer-driven pumps that are very expensive.

It is another object of the present invention to provide a device for the subcutaneous self-administration of drugs or the like, which is capable of being carried on the body of a patient under treatment. The device is associated with a container to contain fluid to be administered to and by the patient and with a remote needle to inject the fluid in the patient. The device comprises coupling means including a one way valve system; a first flexible tube connecting the coupling means to the container; a second flexible tube connecting the downstream side of the coupling means to the needle; the one way valve system incorporating means preventing the back-flow of blood from the patient or administered fluid, and the out flow of the fluid back into the container; a calibrated syringe including a plunger mounted in a syringe holder on the upstream side of the coupling means, the syringe holder acting on the plunger to withdraw a predetermined portion of fluid from the container and thereafter to inject the predetermined portion to the patient.

BRIEF DESCRIPTION OF DRAWINGS

The invention is exemplified by means of a preferred embodiment which is illustrated in the annexed drawings, in which.

DESCRIPTION OF PREFERRED EMBODIMENTS

Figure 1:
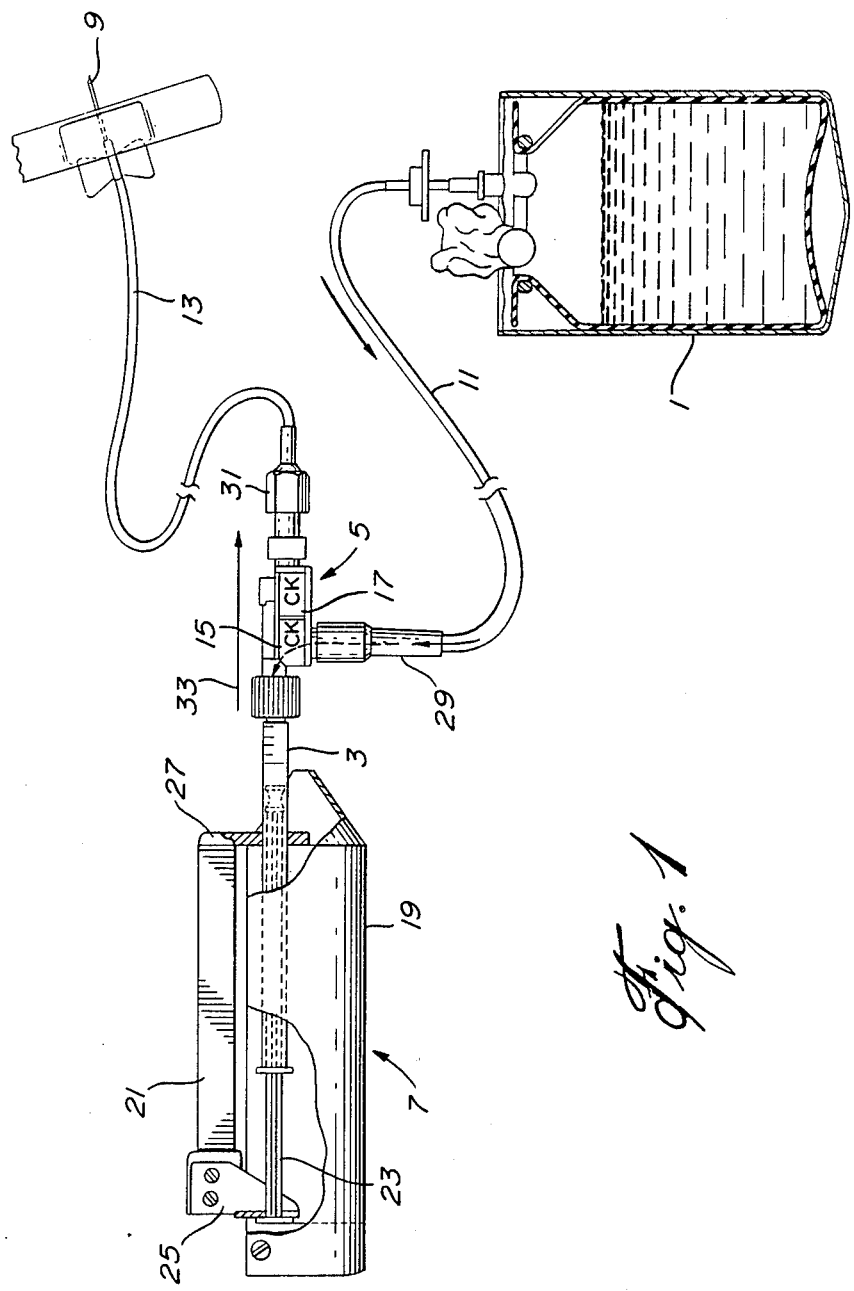
FIG. 1 is a schematic view of the device in the process of withdrawing a treating fluid from a container.
Figure 2:
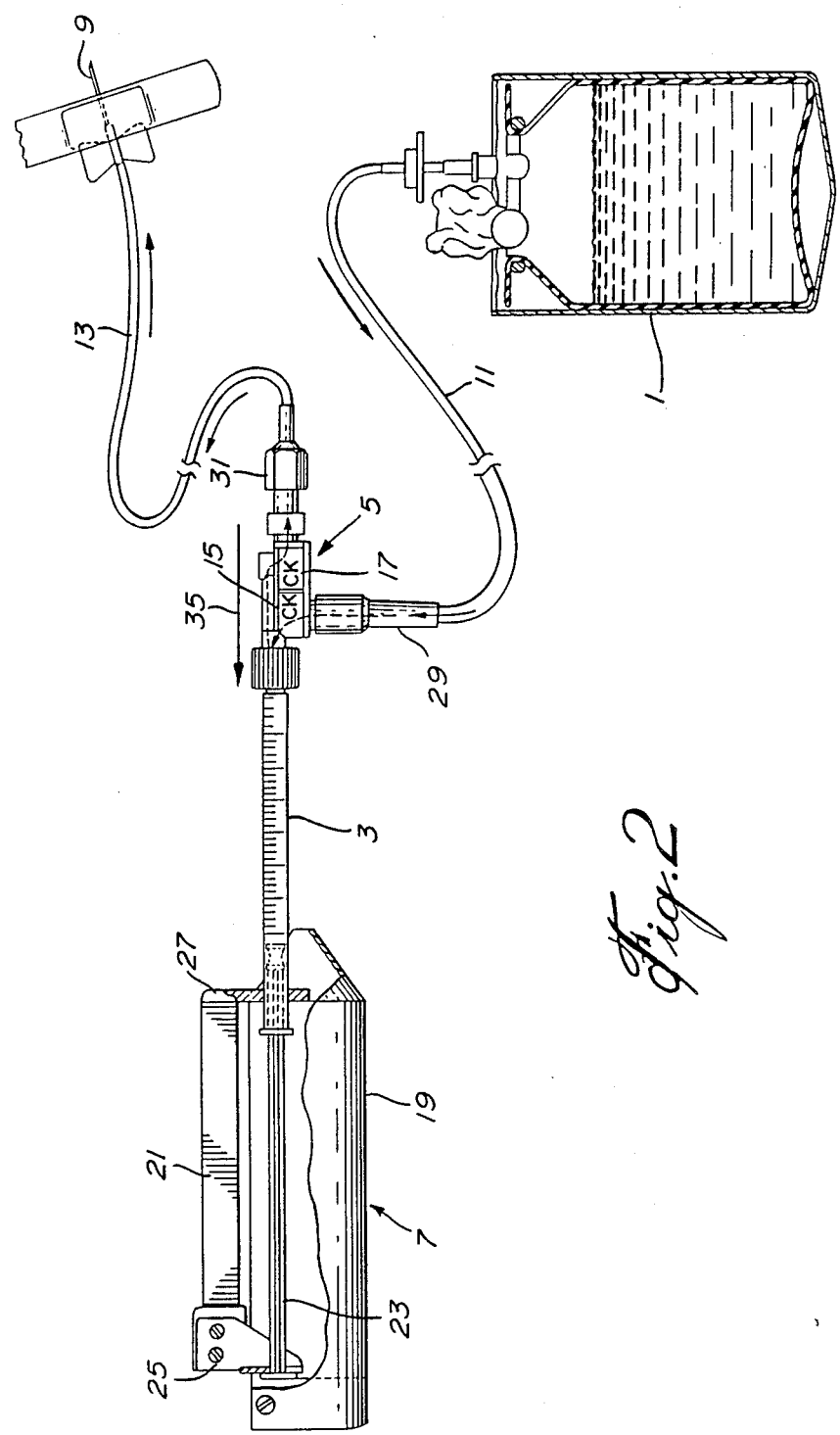
FIG. 2 is another schematic view of the same device, the treating liquid being self-administered by the patent.

With reference to the drawings, it will be seen that the device illustrated mainly consists of a fluid container 1, a syringe 3, a one way valve system 5, a syringe holder 7 and a needle 9. The fluid container 1 is connected to the one way valve system 5 by means of a flexible tube 11, while the needle 9 is connected the same one way valve system 5 by means of a flexible tube 13.

The fluid container 1, needle 9, flexible tubes 11, 13 the one way valve system 5 and the syringe holder 7 are of course conventional and all these parts are well known to those skilled in the art.

The present invention is more specifically designed to be carried on the body (not shown) of a patient by attaching means (not illustrated) well known to those skilled in the art.

The device mainly comprises a syringe holder 7 of specific construction and a one way valve system 5 incorporating two check valves 15 and 17.

The syringe holder includes a channel like tubular shaped member 19 which for design purpose has its forward end conically shaped and its top face longitudinally slotted to receive the syringe 3. A longitudinal bar 21 has its rear end connected to the plunger 23 by means of a connector 25 while its front end has a rider member 27 sitting on the body of the syringe 3 in sliding engagement therewith.

The forward end of the syringe 3 is connected in known manner to the one way valve system 5 and the flexible tubes 11, 13 are respectively connected thereto in known manner at 29, 31.

Check valve 15 prevents the out flow of fluid back into the fluid container 1, during the injection while the check valve 17 prevents the back flow of blood from the patient or administered fluid, while drawing liquid from the container.

In operation, at fixed periods, the patient carrying on his body the device just described merely has to draw a fixed amount of liquid as shown in FIG. 1 by pulling the syringe container 7 away from the valve (see arrow 33). Once the syringe 3 has the proper amount of fluid therein, it is merely necessary to push the syringe holder 7 towards the one way valve system 5 (see arrow 35) and the desired injection is accomplished. Of course, the needle is placed in a proper location at regular intervals, such as one a week, by a doctor or a nurse. Thereafter, the person under medication merely self-administers the drug at predetermined times.

Finally, it may be desirable to affix a counter, such as a golf counter (not shown) to the device in order to account for the number of injections. The counter can be mounted in any manner known to those skilled in the art.

I claim:

1. A device for subcutaneous self-administration of drugs or the like, including means enabling said device to be carried on body of a patient under treatment, said device being associated with a container to contain fluid to be administered to and by said patient and a remote needle to inject said fluid in said patient, said device comprising coupling means including a one way valve system;
a first flexible tube connecting said coupling means to said container;
a second flexible tube connecting downstream side of said coupling means to said needle;
said one way valve system incorporating means preventing back-flow of blood from said patient or administered fluid, and out flow of said fluid back into said container;
a calibrated syringe including a plunger mounted in a syringe holder on upstream side of said coupling means;
said syringe holder having means enabling said plunger to withdraw a predetermined portion of fluid from said container and thereafter to inject all said predetermined portion to said patient.

* * * * *